(12) United States Patent
Gulachenski et al.

(10) Patent No.: US 11,446,474 B2
(45) Date of Patent: *Sep. 20, 2022

(54) REINFORCED BALLOON CATHETER

(71) Applicant: MicroVention, Inc., Aliso Viejo, CA (US)

(72) Inventors: Joseph A. Gulachenski, Trabuco Canyon, CA (US); Roland Guyon, Cowan Heights, CA (US); Cathy Lei, Chino Hills, CA (US); Nelson Peralta, Rancho Santa Margarita, CA (US); Tadele Haile Wolde-Meskel, Cypress, CA (US); Russell Corvese, Huntington Beach, CA (US)

(73) Assignee: Micro Vention, Inc., Aliso Viejo, CA (US)

(*) Notice: Subject to any disclaimer, the term of this patent is extended or adjusted under 35 U.S.C. 154(b) by 203 days.

This patent is subject to a terminal disclaimer.

(21) Appl. No.: 16/447,736

(22) Filed: Jun. 20, 2019

(65) Prior Publication Data

US 2019/0307994 A1 Oct. 10, 2019

Related U.S. Application Data

(63) Continuation of application No. 16/445,983, filed on Jun. 19, 2019, now Pat. No. 11,202,891, which is a continuation of application No. 14/949,824, filed on Nov. 23, 2015, now Pat. No. 10,357,638.

(60) Provisional application No. 62/083,093, filed on Nov. 21, 2014.

(51) Int. Cl.
*A61M 25/10* (2013.01)
*A61M 25/00* (2006.01)

(52) U.S. Cl.
CPC ..... *A61M 25/10185* (2013.11); *A61M 25/005* (2013.01); *A61M 25/0045* (2013.01); *A61M 25/0053* (2013.01); *A61M 25/1006* (2013.01); *A61M 2025/1077* (2013.01)

(58) Field of Classification Search
CPC ........ A61M 25/10185; A61M 25/1006; A61M 25/0045; A61M 25/005; A61M 25/0053; A61M 25/1077; A61M 25/1018; A61M 25/10

See application file for complete search history.

(56) References Cited

U.S. PATENT DOCUMENTS

| | | | |
|---|---|---|---|
| 4,638,805 A | 1/1987 | Powell | |
| 5,224,933 A | 7/1993 | Bromander | |
| 5,728,065 A * | 3/1998 | Follmer | A61M 25/10 604/96.01 |
| 5,836,912 A | 11/1998 | Kusleika | |
| 6,102,891 A | 5/2000 | Maria van Erp | |

(Continued)

OTHER PUBLICATIONS

United States Patent and Trademark Office, Office Action dated Apr. 3, 2018 in U.S. Appl. No. 14/949,824, 13 pages.

(Continued)

*Primary Examiner* — Lauren P Farrar
*Assistant Examiner* — Hamza A Darb
(74) *Attorney, Agent, or Firm* — Inskeep IP Group, Inc.

(57) ABSTRACT

A balloon catheter is described, having a reinforced, coaxial, duel lumen design. At least one of the lumens is formed of a multilayer, tubular element in which one of the layers functions, in part, to provide radial reinforcement to the tubular element.

14 Claims, 12 Drawing Sheets

(56) References Cited

U.S. PATENT DOCUMENTS

| | | | |
|---|---|---|---|
| 7,641,631 B2 * | 1/2010 | Chin | A61M 25/0075 604/96.01 |
| 10,357,638 B2 | 7/2019 | Gulachenski et al. | |
| 2005/0065544 A1 | 3/2005 | Yamaguchi et al. | |
| 2011/0112567 A1 | 5/2011 | Lenker et al. | |
| 2012/0203173 A1 | 8/2012 | Davies, Jr. et al. | |
| 2012/0245521 A1 | 9/2012 | Gulachenski et al. | |

OTHER PUBLICATIONS

United States Patent and Trademark Office, Final Office Action dated Nov. 15, 2017 in U.S. Appl. No. 14/949,824, 12 pages.
United States Patent and Trademark Office, Office Action dated May 9, 2017 in U.S. Appl. No. 14/949,824, 13 pages.
United States Patent and Trademark Office, Office Action dated Sep. 21, 2016 in U.S. Appl. No. 14/949,824, 6 pages.
WIPO, U.S. International Search Authority, International Search Report and Written Opinion dated Feb. 2, 2016 in International Patent Application No. PCT/US2015/06228, 6 pages.
United States Patent and Trademark Office, Office Action dated Feb. 25, 2021 in U.S. Appl. No. 16/445,983, 12 pages.

* cited by examiner

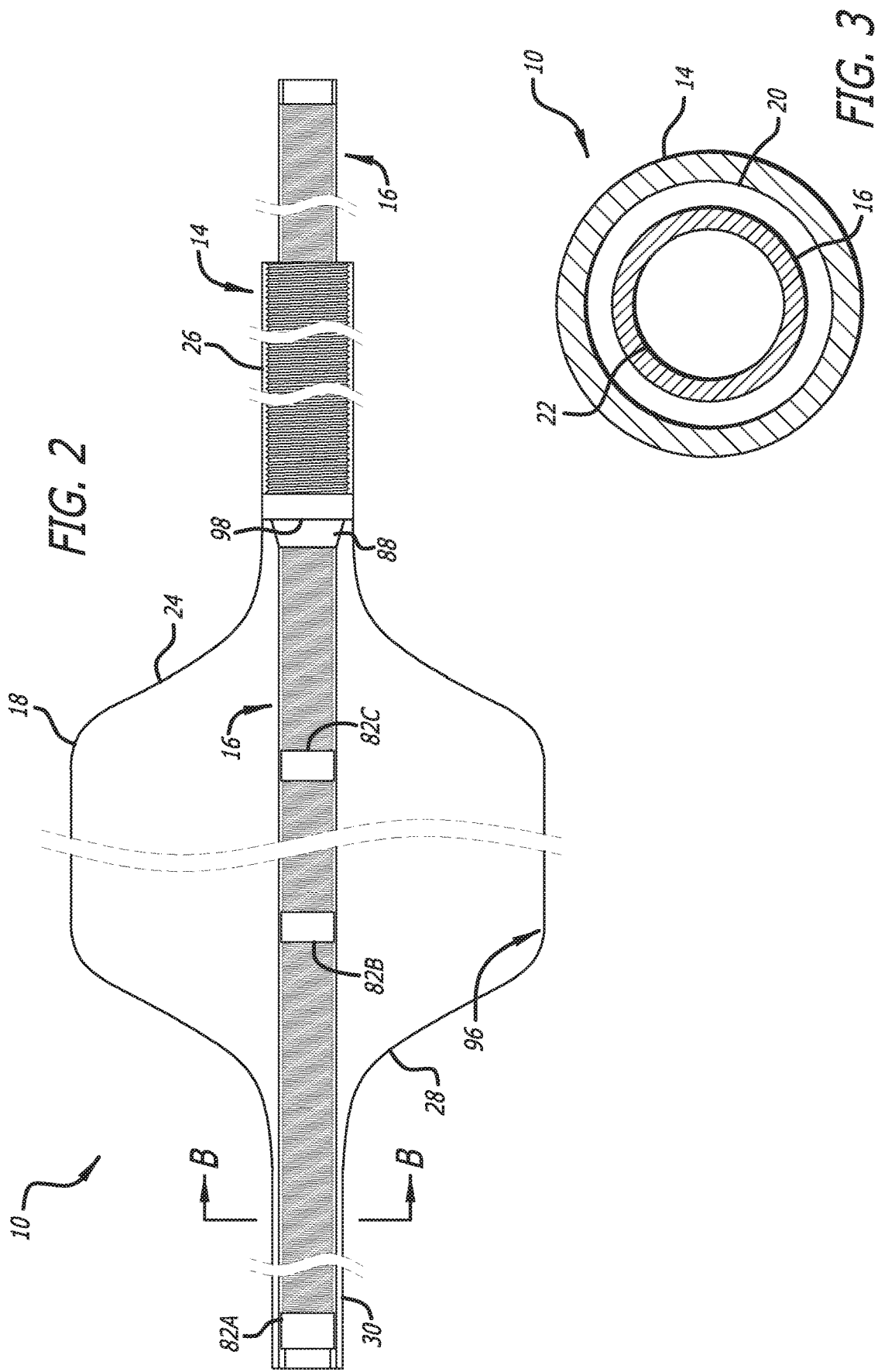

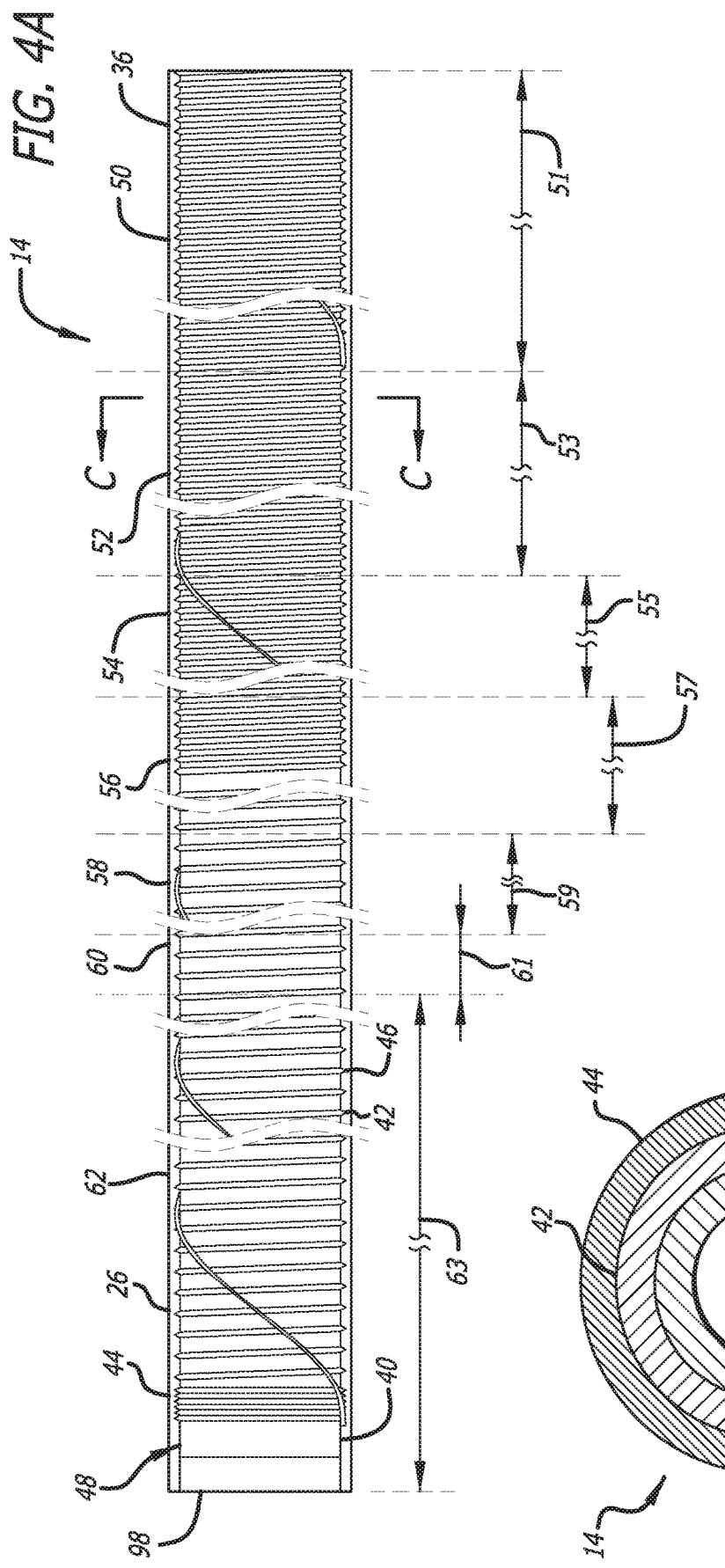

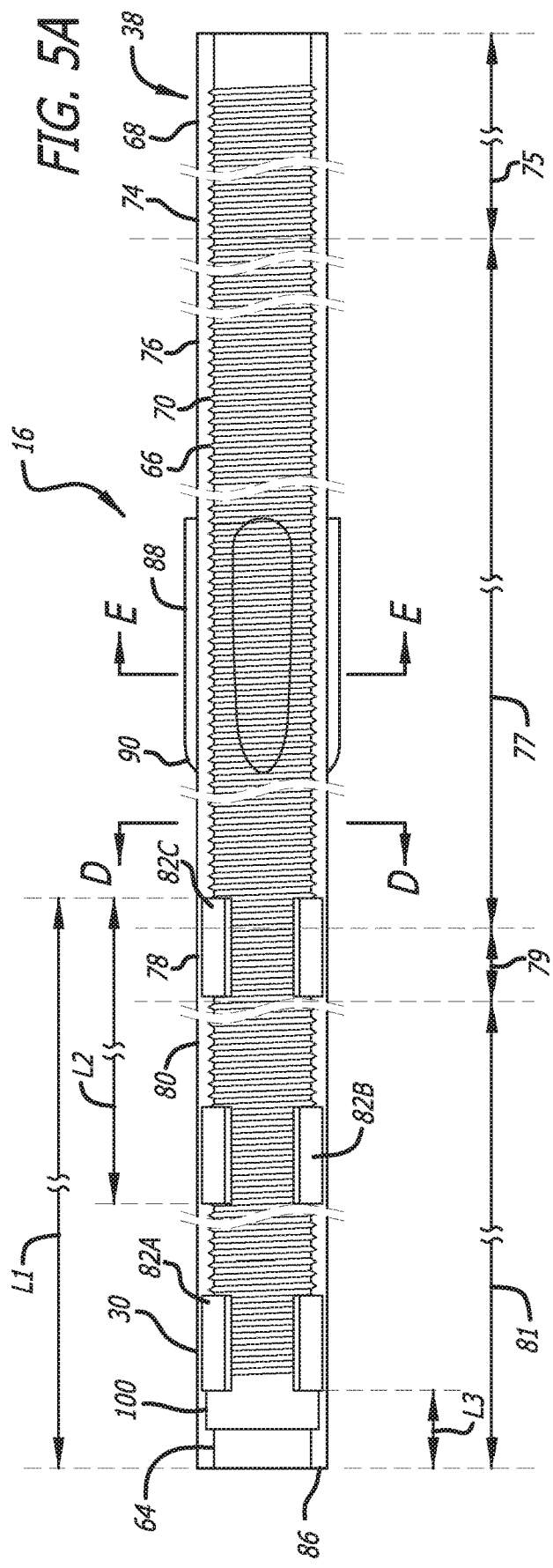

REINFORCED BALLOON CATHETER

RELATED APPLICATIONS

This application is a continuation of and claims priority to patent application Ser. No. 16/445,983, filed Jun. 19, 2019, entitled Improved Reinforced Balloon Catheter, which is a continuation of and claims priority to patent application Ser. No. 14/949,824, filed Nov. 23, 2015, entitled Improved Reinforced Balloon Catheter (now U.S. Pat. No. 10,357, 638B2, issued on Jul. 23, 2019), which claims benefit of and priority to U.S. Provisional Application Ser. No. 62/083,093 filed Nov. 21, 2014 entitled Improved Reinforced Balloon Catheter, all of which are hereby incorporated herein by reference in their entireties.

BACKGROUND OF THE INVENTION

Balloon catheters are increasingly being employed to conduct neurological procedures in patients. However, the design parameters for balloon catheters intended for use in neurological procedures are significantly different than the design parameters for balloon catheters used in non-neurological procedures such as cardiological procedures. For example, the width of the circulatory system within the neuroanatomy is significantly smaller and more tortuous than the circulatory system in other parts of the body. In order to access the smaller and more tortuous regions of the neuroanatomy, it is necessary to minimize the outer diameter of the balloon catheter while simultaneously maintaining the pushability and trackability of the catheter.

In order to minimize the outer diameter, current balloon catheters intended for neurological procedures employ a non-reinforced, single lumen, over-the-wire design. Accordingly, these balloon catheters are prone to several problems. First, the non-reinforced lumen is susceptible to ovalizing and/or kinking which, in turn, hinders advancement of the catheter over the guidewire, as well as deflation of the balloon. Second, the single lumen is in communication with the arterial blood flow. As the guidewire and balloon catheter are manipulated through the circulatory system, blood is withdrawn into the single lumen of the balloon catheter. Blood may thereby enter the balloon during inflation and cause (1) poor imaging of the balloon, for example, poor fluoroscopic imaging; (2) poor passage of the balloon through the circulatory system due to the premature inflation of the balloon; and (3) poor deflation of the balloon due to blood coagulation in the balloon inflation/deflation port. An additional disadvantage of single lumen balloon catheters is that the interference fit of the guidewire and inflation seal of the balloon may result in removal or peeling of the hydrophilic coating of the guidewire.

In order to minimize the outer diameter, current balloon catheters intended for neurological procedures are also typically designed to work with only a narrow gauge guidewire that is supplied by a manufacturer along with the balloon catheter. The current balloon catheters employ guidewires having diameters in the range of 0.010 to 0.012 inches. These relatively narrow guidewires are soft and, therefore, are very difficult to maneuver through the small, tortuous neuroanatomy.

What is needed in the field is a balloon catheter that is operable to use with larger gauge guidewires; resists ovalizing and kinking of the inflation and guidewire lumen(s); and deploys with improved pushability and trackability.

SUMMARY OF THE INVENTION

In one embodiment, the present invention includes a balloon catheter that is operable to use with large gauge guidewires, resists ovalizing and kinking of the inflation and guidewire lumen(s), and deploys with improved pushability and trackability.

The present invention according to another embodiment provides a balloon catheter that employs a reinforced, coaxial, duel lumen design. In certain embodiments, the lumen are formed of a multilayer, tubular element in which one of the layers functions, in part, to provide radial reinforcement to the tubular element.

In another embodiment of the present invention, the distal portion of an outer lumen is locked or fixed to a portion of an inner lumen. A proximal portion of a balloon is attached to a distal portion of the outer lumen and a distal portion of the balloon is attached to a distal portion of the inner lumen.

In another embodiment, a fluid flow passage is provided between the outer lumen and an interior volume of the balloon, and a passage exclusive to gas or air is formed from the interior volume of the balloon longitudinally through a distal portion of the balloon catheter.

In certain other embodiments, de-airing channels or features are employed between an exterior surface of the inner lumen and an interior surface of the balloon in order to facilitate purging of gas from the inflation passageway of the balloon catheter.

In another embodiment, a tapered inflation lumen is utilized. In another embodiment a tapered guidewire lumen is utilized. In another embodiment, both the inflation lumen and guidewire lumen are tapered. The taper can be continuous throughout the lumen(s), or localized within a particular region of the lumen(s).

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 2 is a partial elevation view of a balloon catheter according to one embodiment of the present invention.

FIG. 3 is a cross-sectional view taken along line A-A of FIG. 1 of a balloon catheter according to one embodiment of the present invention.

FIG. 4A is a partial elevation view of an outer assembly of a balloon catheter according to one embodiment of the present invention.

FIG. 4B is a cross-sectional view taken along line C-C of FIG. 4A of an outer assembly of a balloon catheter according to one embodiment of the present invention.

FIG. 5A is a partial elevation view of an inner assembly of a balloon catheter according to one embodiment of the present invention.

FIG. 5B is a cross-sectional view taken along line D-D of FIG. 5A of an inner assembly of a balloon catheter according to one embodiment of the present invention.

DESCRIPTION OF EMBODIMENTS

Figure 1:
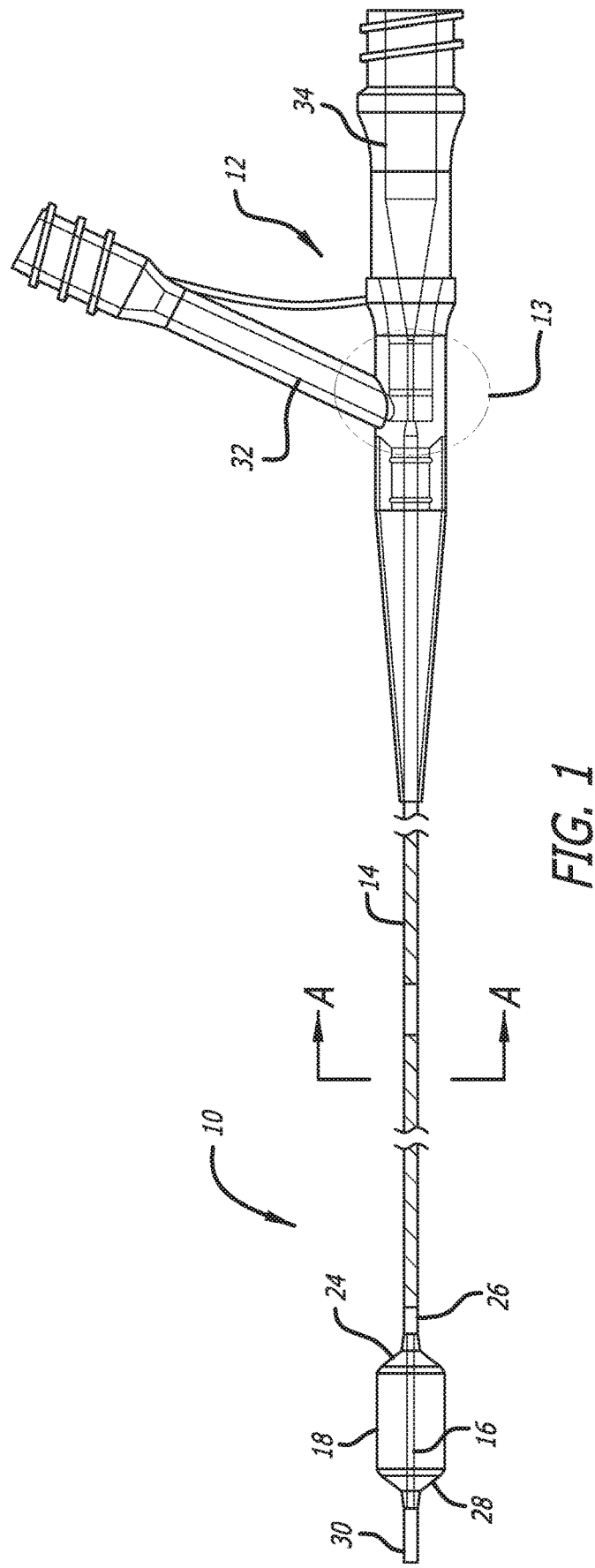
FIG. 1 is an elevation view of a balloon catheter according to one embodiment of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The balloon catheter of the present invention addresses many of the shortcomings of the current balloon catheters intended for use in neurological procedures. Broadly speaking, the balloon catheter of the present invention employs a reinforced, co-axial, duel lumen design. The inner most lumen is operable to serve, among other functions, as a guidewire lumen for over-the-wire type procedures. The outer lumen is operable to serve as an inflation lumen for one or more balloons positioned along the length of the balloon catheter. Each lumen is formed by a multilayer, tubular element in which one of the layers, for example a middle layer in a three-layer embodiment, functions in part to provide radial reinforcement to the tubular element. Accordingly, the balloon catheter of the present invention is operable with larger gauge guidewires; resists ovalizing and kinking of the inflation and guidewire lumens; and deploys with improved pushability and trackability over current balloon catheters intended for use in neurological procedures.

Figure 6:
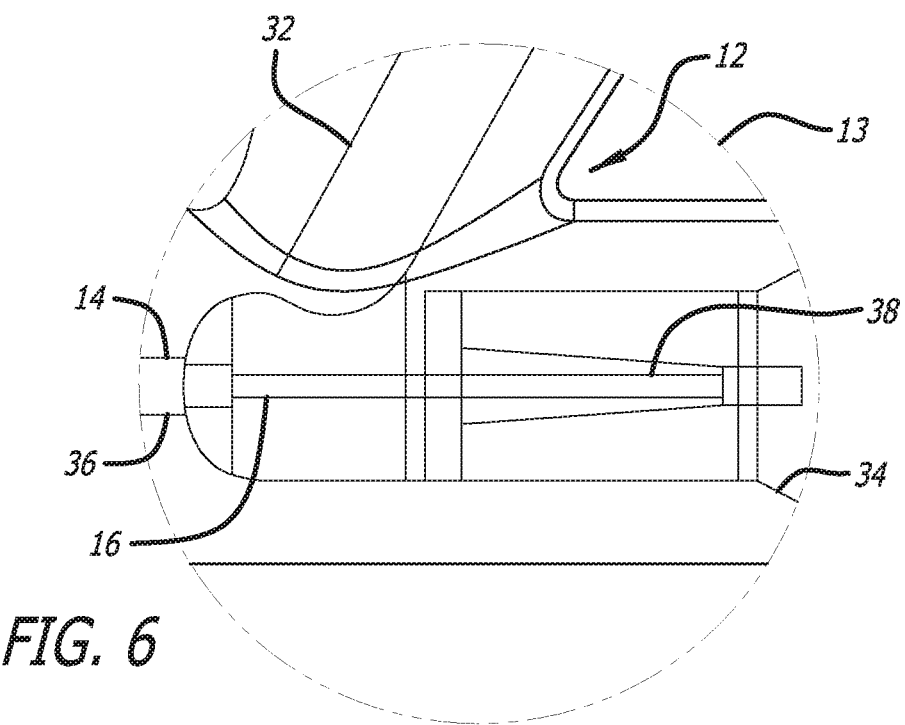
FIG. 6 is an expanded view of region 13 indicated in FIG. 1 of a balloon catheter according to one embodiment of the present invention.

With reference to FIGS. 1-3 and 6, a balloon catheter 10 according to one embodiment of the present invention comprises a hub 12, a balloon 18, and an outer assembly 14 having a lumen 20 through which an inner assembly 16 is co-axially positioned. As best shown in FIG. 6, an expanded view of region 13 indicated in FIG. 1, a proximal portion 36 of the outer assembly 14 is associated with an inflation lumen 32 of the hub 12. A proximal portion 38 of the inner assembly 16 extends proximally from the lumen 20 of the outer assembly 14 and is associated with a guidewire port 34 of the hub 12. At an opposite end of the catheter, a proximal portion 24 of the balloon 18 is associated with a distal portion 26 of the outer assembly 14, and a distal portion 28 of the balloon 18 is associated with a distal portion 30 of the inner assembly 16. Alternatively stated, the opposite ends of the balloon 18 span between the distal portion 26 of the outer assembly 14 and the distal portion 30 of the inner assembly 16.

As shown in FIGS. 4A and 4B, the outer assembly 14 is a tubular structure having a multilayer wall; an inner layer 40, middle layer 42, and outer layer 44. The inner layer 40 of the outer assembly 14 is formed of a longitudinally continuous or segmented tubular element. In embodiments in which the inner layer 40 of the outer assembly 14 is formed of longitudinally segmented tubular elements the individual segments may be fabricated from the same or different materials and may be attached to one another by welding, fusing, adhering, melting, or other polymerizing or non-polymerizing methods. The inner layer 40 of the outer assembly 14 is fabricated from one or more different polymeric materials, or, alternatively, the inner layer 40 of the outer assembly 14 is formed of a single etched polytetrafluoroethylene, PTFE, tube. While a variety of materials are contemplated for use in fabricating the inner layer 40 of the outer assembly 14, of particular importance is the feature that the material from which the inner layer 40 is formed has a higher melting temperature than the temperature employed to fuse or otherwise attach the outer layer 44 to the inner layer 40 and middle layer 42 of the outer assembly 14.

In one embodiment of the present invention, the middle layer 42 of the outer assembly 14 comprises a wire 46 wound in a coil-like form around the outer surface 48 of the inner layer 40 of the outer assembly 14. The wire 46 may be wound in a single layer from one end of the inner layer 40 to the other end to form a coil-like structure or, alternatively, may be wound repeatedly from one end of the inner layer 40 to the other end to form a multilayer coil-like form, as shown in FIG. 4A. In embodiments employing the middle layer 42 having a multilayered coil-like form, the different windings may be formed from a single or multiple independent wires 46. The wire 46 may have a circular, rectangular, triangular, or flattened ribbon-like cross-sectional shape, or combinations thereof. The wire 46 is fabricated from a variety of polymeric and/or metallic materials, for example stainless steel. The wire 72 has a diameter that is variable or consistent along the length of the wire 72. For example, the wire 72 may have a diameter of approximately 0.001 inches. It is also contemplated that the middle layer 42 be formed of a mesh, a braid, and/or an interweaving of one of more wires 46.

The pitch of the winding of the wire 46 may be either consistent or varied along the length of the inner layer 40. For example, a first proximal segment of the winding may have a pitch of approximately 0.003 inches, a second more distal segment may have a pitch of approximately 0.0035 inches, a third more distal segment may have a pitch of approximately 0.004 inches, a fourth more distal segment may have a pitch of approximately 0.0045 inches, a fifth more distal segment may have a pitch of approximately 0.005 inches, and a sixth more distal segment may have a pitch of approximately 0.001 inches. In embodiments employing the middle layer 42 having a multilayered coil-like form the outer most winding may, for example, have a pitch of approximately 0.100 inches.

In one embodiment of the present invention, the outer layer 44 of the outer assembly 14 comprises a longitudinally continuous or segmented tubular element. The outer layer 44 of the outer assembly 14 is formed of longitudinally segmented, non-heat shrinkable, tubular elements. The individual segments may be fabricated from the same or different materials and may be attached to one another by welding, fusing, adhering, melting, or other polymerizing or non-polymerizing methods, or combinations thereof.

In one embodiment, the outer layer 44 of the outer assembly 14 is fabricated from multiple different polymeric tubular segments. For example, a proximal segment 50 of the outer layer 44 of the outer assembly 14 may be formed of a tubular polyamide such as Girlamid L25. The proximal segment 50 has a length 51, of, for example, approximately 110 centimeters. A second more distal segment 52 may be formed of a tubular poly ether block amide such as Pebax 72D. The second more distal segment 52 has a length 53, of, for example, approximately 10 centimeters. A third more distal segment 54 may be formed of a tubular poly ether block amide such as Pebax 63D. The third more distal segment 54 has a length 55, of, for example, approximately 5 centimeters. A forth more distal segment 56 may be formed of a tubular poly ether block amide such as Pebax 55D. The forth more distal segment 56 has a length 57, of, for example, approximately 20 centimeters. A fifth more distal segment 58 may be formed of a tubular poly ether block amide such as Pebax 45D. The fifth more distal segment 58 has a length 59, of, for example, approximately 10 millimeters. A sixth more distal segment 60 may be formed of a polyolefin such a Plexar. The sixth more distal segment 60 has a length 61, of, for example, approximately 2 millimeters. A distal most segment 62 may be formed of a polyolefin such an Engage 8003. The distal most segment 62 has a length 63 of, for example, approximately 13 centimeters.

The outer assembly 14 may be fabricated by first wrapping the wire 46 around the inner layer 40 thereby forming the middle layer 44. The tubular segment or segments of the outer layer 44 are then slid over the middle layer 42. A heat shrinkable tube of, for example, fluorinated ethylene propylene, FEP, is then slid over the outer layer 44. The FEP is heated so as to deliver heat to the outer layer 44, and the outer layer 44 then softens to encapsulate the wire 46. The FEP tube is then removed from the outer layer 44.

In one embodiment of the present invention, the outer diameter of the outer layer 44 of the outer assembly 14 is in the range of 0.03 to 0.040 inches. The lumen 20 of the outer assembly 14 may have a diameter between 0.020 to 0.029 inches. In one embodiment, the lumen 20 of the outer assembly 14 may have a diameter of approximately 0.0285 inches.

As shown in FIGS. 5A and 5B, the inner assembly 16 is a tubular structure having a multilayer wall formed of an inner layer 64, middle layer 66, and outer layer 68. The inner layer 64 of the inner assembly 16 is formed of a longitudinally continuous or segmented tubular elements. In embodiments in which the inner layer 64 of the inner assembly 16 is formed of longitudinally segmented tubular elements, the individual segments may be fabricated from the same or different materials and may be attached to one another by welding, fusing, adhering, melting, or other polymerizing or non-polymerizing methods, or combinations thereof. The inner layer 64 of the inner assembly 16 is fabricated from one or more different polymeric materials, or, alternatively, the inner layer 64 of the outer assembly 14 is formed of a single, non-segmented, etched polytetrafluoroethylene, PTFE, tube. While a variety of materials are contemplated for use in fabricating the inner layer 64 of the inner assembly 16, it is important to employ a material that has a higher melting temperature than the temperature employed to fuse or otherwise attach the outer layer 68 to the inner layer 64 and middle layer 66 of the inner assembly 16. It is also desirable to employ a material that has a relatively low co-efficient of friction.

In one embodiment of the present invention, the middle layer 66 of the inner assembly 16 comprises a wire 70 wound in a coil-like form around the outer surface 72 of the inner layer 64 of the inner assembly 16. The wire 72 may be wound in a single layer from one end of the inner layer 64 to the other or, alternatively, may be wound repeatedly from one end of the inner layer 64 to the other to form a multilayer coil-like form, as shown in FIG. 4A regarding wire 46 of the outer assembly 14. In embodiments employing the middle layer 66 having a multilayered coil-like form, the different coils may be formed from a single or multiple independent wires 72. The wire 72 may have a circular, rectangular, triangular, flattened, ribbon-like cross-sectional shape, or a combination thereof. The wire 72 may be fabricated from a variety of metallic and/or polymeric materials, for example stainless steel. The wire 72 may have a diameter that is variable or consistent along the length of the wire 72. For example, the wire 72 may have a diameter of approximately 0.001 inches. It is also contemplated that the middle layer 42 may be formed of a mesh or interweaving of one of more wires 46.

The pitch of the winding of the wire 72 may be either consistent or varied along the length of the inner layer 64 of the inner assembly 16. For example, a first proximal segment of the wire 72 winding may have a pitch of approximately 0.003 inches, a second more distal segment may have a pitch of approximately 0.003 inches, and a third most distal segment may have a pitch of approximately 0.001 inches.

As shown in FIGS. 2 and 5A, in one embodiment of the present invention, one or more marker bands 82A, 82B, and 82C are placed, for example, over the wire 70 forming the middle layer 66 of the inner assembly 16. The marker bands 82A, 82B, and 82C comprise a radiopaque material such as gold, platinum, or silver, and are used for determining the location of the balloon catheter 10 within a patient. In certain embodiments of the present invention the maker band 82A may be placed a distance L3 proximate to a distal end 86 of the inner assembly 16. For example, the distance L3 may be 5 millimeters. In one embodiment, instead of marker bands, marker coils may be used. In one embodiment, two sets of marker coils are used where one coil overlaps another to augment the radiopacity of the marker elements.

The marker bands 82B and 82C may be positioned further proximal of the marker band 82A so as to indicate or mark the proximal portion 24 and the distal portion 28 of the balloon 18. It will be understood that the exact placement of the marker bands 82B and 82C relative to the distal end 86 of the inner assembly 16 will depend on the dimensions of the balloon 18 employed in the balloon catheter 10.

For example, in an embodiment employing a balloon 18 of 10 millimeters in length, a proximal end 84 of the marker band 82C is a distance L1 from the distal end 86 of the inner assembly 16. For example, the distance L1 may be approximately 19.5 millimeters. Opposite ends of the marker bands 82B and 82C are a distance L2 from one another. For example, the distance L2 may be 10 millimeters. In an embodiment employing a balloon 18 of 20 millimeters in length, the distance L1 is, for example, approximately 29.5 millimeters, and the distance L2 is, for example, 20 millimeters. In another embodiment, the marker band 82C may be placed directly underneath inflation plug 88.

In one embodiment of the present invention, the outer layer 68 of the inner assembly 16 comprises a longitudinally continuous or segmented tubular element. Preferably the outer layer 68 of the inner assembly 16 is formed of series of longitudinally segmented, non-heat shrinkable, tubular elements. The individual segments are fabricated from the same or different materials and may be attached to one another by welding, fusing, adhering, melting, or other polymerizing or non-polymerizing methods. Preferably, the outer layer 68 of the inner assembly 16 is fabricated from multiple different polymeric tubular segments. For example, a proximal segment 74 of the outer layer 68 of the inner assembly 16 may be formed of a tubular poly ether block amide such as Pebax 63D. The proximal segment 74 has a length 75 of, for example, approximately 150 centimeters. A second more distal segment 76 may be formed of a tubular poly ether block amide such as Pebax 45D. The second more distal segment 76 has a length 77 of, for example, approximately 10 centimeters. A third more distal segment 78 may be formed of a polyolefin such as Plexar 3080. The third more distal segment 78 has a length 79 of, for example, approximately 2 millimeters. A distal most segment 80 may be formed of a polyolefin such as Engage 8003, and have a length 81 of, for example, approximately 5 centimeters.

The inner assembly 16 may be fabricated by first wrapping the wire 70 around the inner layer 64 thereby forming the middle layer 66. Next, the marker bands 82A, 82B, and 82C are placed over or within the middle layer 66, and the tubular segment or segments of the outer layer 68 are then slid over the marker bands 82A, 82B, and 82C and the middle layer 66. A heat shrinkable tube of, for example, fluorinated ethylene propylene, FEP, is then slid over the outer layer 68. The FEP is heated so as to deliver heat to the outer layer 68, thereby softening the outer layer 68 so as to encapsulate the wire 70 forming the middle layer 66. The FEP tube is then removed from the outer layer 68.

In one embodiment of the present invention, the wire 70 forming the middle layer 66 of the inner assembly 16 may terminate proximal of the distal end 86 of the outer assembly 16. A tubular element 100 may be employed in all or a portion of the length between the distal end 86 and the point at which the wire 70 terminates. The tubular element 100 may, for example, be formed of a crosslinked polyolefin tube having a length of approximately 5 millimeters.

In one embodiment of the present invention, the outer diameter of the outer layer 68 of the inner assembly 16 is in the range of 0.015 to 0.025 inches, and more preferably in the range of 0.020 to 0.0225 inches.

Figure 5C:
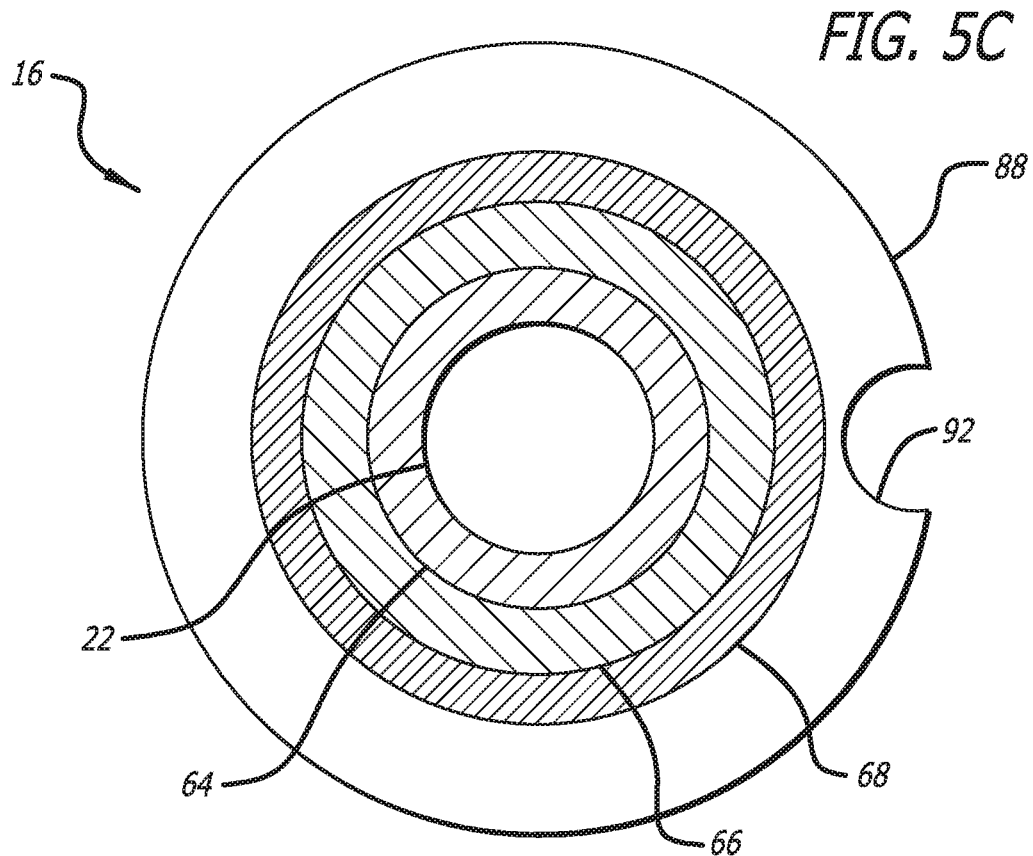
FIG. 5C is a cross-sectional view taken along line E-E of FIG. 5A of an inner assembly of a balloon catheter according to one embodiment of the present invention.

As shown in FIGS. 2, 5A, and 5C, in one embodiment of the present invention, the inner assembly 16 may further comprise an inflation plug 88. The inflation plug 88 is formed of a tubular segment of material having a wall of either uniform or asymmetric thickness. In some embodiments, the inflation plug may have a durometer ranging between 18A to 55D. The inflation plug 88 may, for example be formed of a poly ether block amide such as Pebax 55D. The inflation plug may, for example, be approximately 5 millimeters in length and a distal end 90 of the inflation plug 88 may, for example, be positioned approximately 4 millimeters from the proximal end 84 of the marker band 82C. An outer dimension or diameter of the inflation plug 88 is large enough so that the inflation plug 88 may not completely pass into the lumen 20 of the outer assembly without significant force. The inflation plug 88 may be formed on the inner assembly 16 as described above regarding the formation of the outer layer 68 of the inner assembly 16.

As shown in FIG. 5C, the inflation plug 88 may comprise one or more passages or channels 92 formed longitudinally along the length of the inflation plug. The channel 92 may be formed by placing a mandrel longitudinally along the outside surface of the inflation plug 88 prior to sliding the heat shrinkable tube of, for example, FEP over the inflation plug 88. When the FEP is heated so as to deliver heat to the inflation plug 88, the mandrel melts into the inflation tube thereby the channel 92 within the inflation plug 88. The FEP tube is then removed from the inflation plug 88.

The inflation plug 88 functions, in part, to longitudinally lock the inner assembly 16 to the outer assembly 14 so as to prevent changes in the length of the distal extension of the distal portion 30 of the inner assembly 16 relative to a distal end 98 of the outer assembly 14 due to the inflation and orientation of the balloon 18 during a procedure. The passage or channel 92 formed in the plug 88 allows for fluid communication between the lumen 20 of the outer assembly and an interior volume of the balloon 18.

As shown in FIGS. 3, 5B, 5C, and 7, the inner assembly 16 comprises an inner lumen 22. The lumen functions as a guidewire lumen for over-the-wire procedures. The lumen 22 of the inner assembly 16 may have a diameter of at least approximately 0.0165 inches. Accordingly, the balloon catheter 10 of the present invention may be used with guidewires having a larger diameter than the guidewires supplied with current balloon catheters intended for use in neurological procedures. For example the present balloon catheter 10 may be used with a guidewire having a diameter of 0.014 inches. This feature allows a physician to more easily access a neuroanatomical target, such as an aneurysm, since the relatively larger guidewire provides more support for the balloon catheter 10 over which to track.

Additionally, the guidewire may be removed from the lumen 22 after placement of the balloon catheter within a patient and the lumen 22 may serve as a functional lumen for passage of additional medical devices or substances to the target location within the patient.

It will be understood that it is generally beneficial for the outer assembly 14 and the inner assembly 16 to be more flexible at their distal portions than their proximal portions. Furthermore, it is contemplated that the distal portions of the outer assembly 14 and/or the inner assembly 16 may be pre-shaped or operable to be shaped by a physician prior to initiating a procedure using, for example, steam shaping techniques.

As shown in FIGS. 1 and 6, the proximal portion 36 of the outer assembly 14 terminates distally of the proximal portion 38 of the inner assembly 16. Accordingly, the lumen 20 of the outer assembly is in communication with the inflation port 32. FIGS. 1 and 6 also show that the proximal portion 38 of the inner assembly 16 extends proximally beyond the proximal portion 36 of the outer assembly 14 and is associated with the guidewire port 34 of the hub 12. Accordingly, the lumen 22 of the inner assembly and the guidewire port 34 of the hub 12 together form a substantially continuous lumen through which a guidewire or other medical device may pass. The outer assembly 14 and the inner assembly 16 may be attached to the hub 12 by various methods, including welding, fusing, adhering, melting, or other polymerizing or non-polymerizing method, or combinations thereof. It is noted that this configuration of the hub 12 and association of the hub 12 with the outer assembly 14 and the inner assembly 16 advantageously provides for the isolation of the lumen 22 of the inner assembly 16 from the lumen 20 of the outer assembly 14. The isolation of these lumens and their functionality serves, in part, to address many of the shortcomings described above regarding the current single lumen balloon catheters intended for neurological procedures.

As shown in FIGS. 1 and 2, the proximal portion 24 of the balloon 18 is associated with the distal portion 26 of the outer assembly 14, and the distal portion 28 of the balloon 18 is associated with the distal portion 30 of the inner assembly 16. The balloon 18 may be attached to the distal portion 26 of the outer assembly 14 and the distal portion 30 of the inner assembly 16 by various methods including welding, fusing, adhering, melting, or other polymerizing or non-polymerizing methods and combinations thereof. In certain embodiments, the distal portion of the balloon 18 covers and extends to the distal end 86 of the inner assembly 16. The balloon 18 may, for example, be formed of Polyblend 45A or other polymeric elastomeric material. The balloon 18 may have an outer diameter of up to approximately 15 millimeters and a length in the range of 5 to 50 millimeters and, preferably a length in the range of 10 to 20 millimeters.

Figure 7:
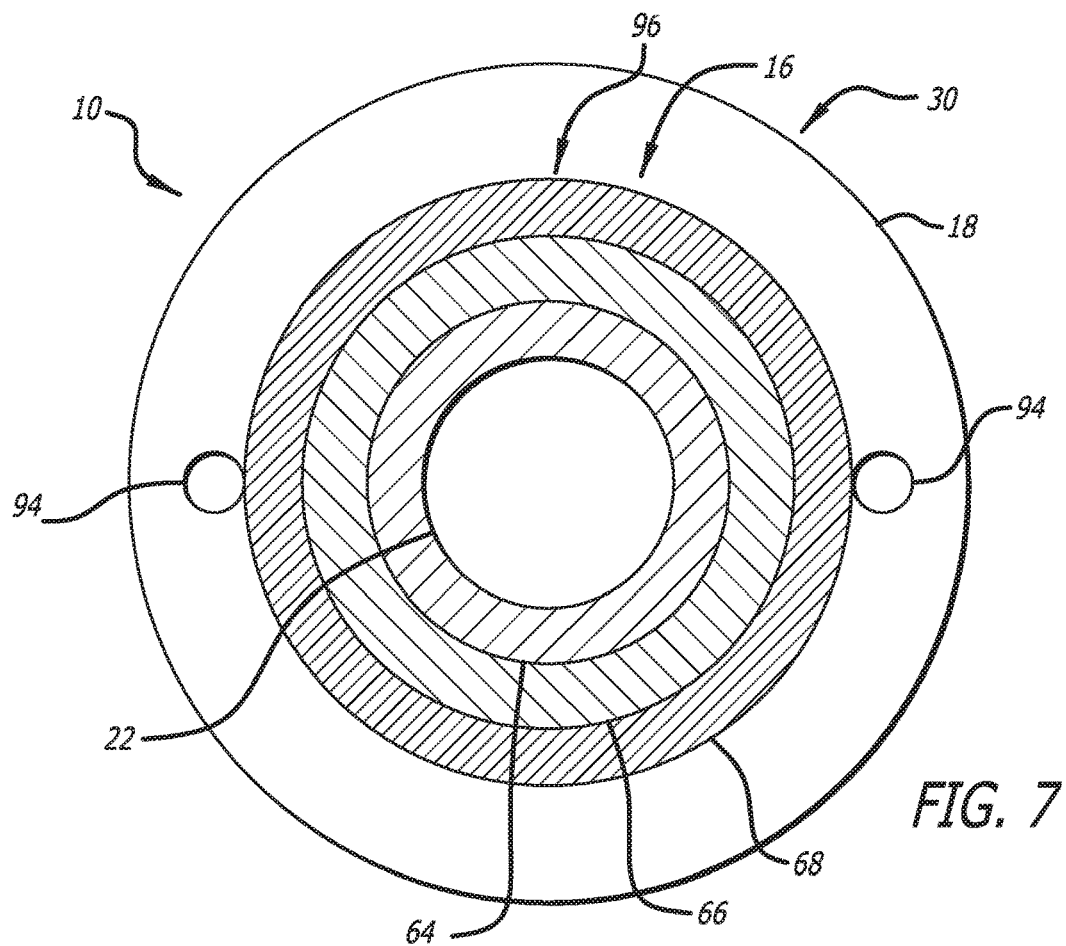
FIG. 7 is a cross-sectional view taken along line B-B of FIG. 2 of an inner assembly of a balloon catheter according to one embodiment of the present invention.

As shown in FIG. 7, in one embodiment of the present invention, one or more air purge ports 94 are employed at the interface of the distal portion 30 of the inner assembly 16 and the distal portion 28 of the balloon 18. The air purge ports 94 are formed by placing one of more mandrels having diameters in the range of 0.0005 to 0.030 inches on the outer surface of the outer layer 68 of the inner assembly 16. An interior surface 96 of the balloon 18 is then attached over the mandrels to the outer layer 68 of the inner assembly 16. After the balloon 18 is attached to the distal portion 30 of the inner assembly 16 the mandrels are removed. Accordingly, flow paths large enough for the passage of gas and small enough to seal against the passage of liquids are formed.

The air purge ports 94 function to facilitate removal of air from the lumen 20 and balloon 18 prior to initiating a medical procedure. With current co-axial balloon catheters, it is very difficult to remove all of the air from the inflation/deflation lumen prior to initiating a medical procedure. Physicians typically must remove the air from a balloon catheter through several minutes of aspiration or suction through the inflation/deflation lumen. Air that is not removed will show in images taken during the procedure and may obscure details that the physician may otherwise need to observe in order to perform the procedure.

In contrast, the air purge ports 94 of the present invention allow a user to more effectively and more efficiently remove air from the lumen 20, the inflation/deflation lumen. In practice, prior to initiating the procedure, a physician positions the distal end of the balloon catheter 10 higher than the proximal end and then inject a balloon inflation medium, such as contrast medium or saline, through the inflation port 32 and associated lumen 20. As the inflation medium fills the lumen 20, air is forced out the air purge ports 94 until no air remains within the lumen 20 or balloon 18. The physician may repeat the process as needed to ensure that all air is removed from the lumen 20 of the outer assembly 14 and balloon 18.

Figure 8:
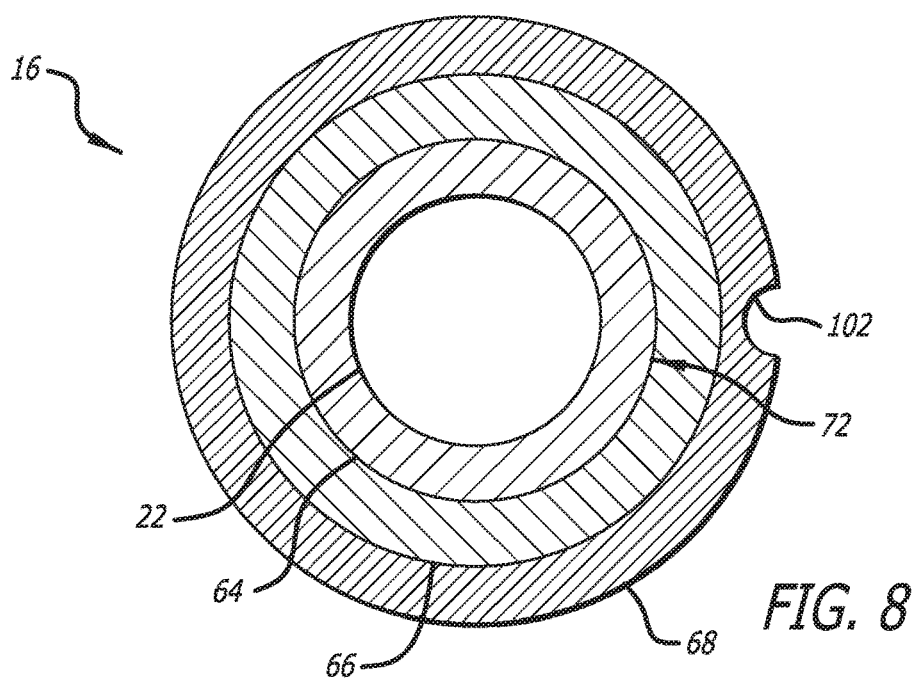
FIG. 8 is a cross-sectional view taken along line D-D of FIG. 5A of an inner assembly of a balloon catheter according to one embodiment of the present invention.
Figure 9:
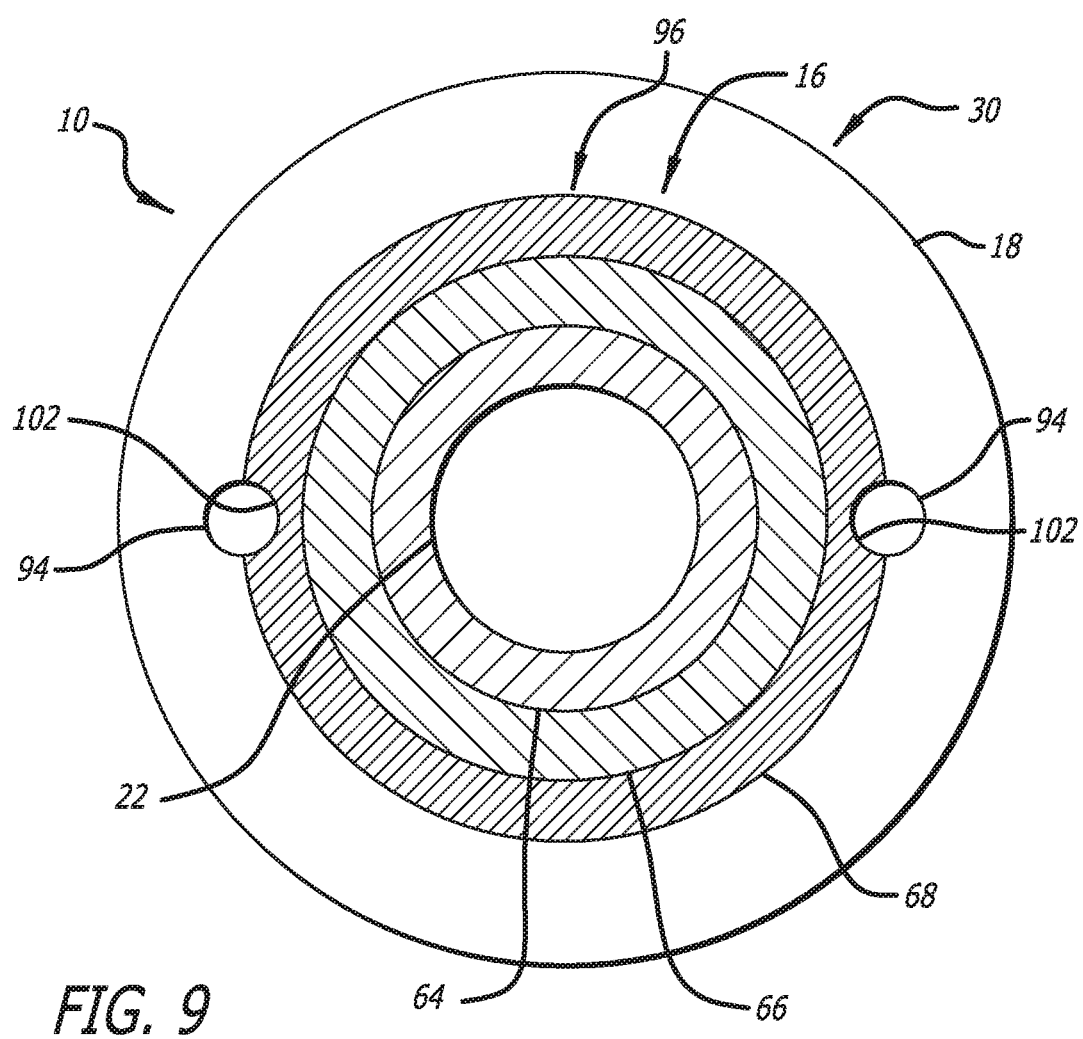
FIG. 9 is a cross-sectional view taken along line B-B of FIG. 2 of an inner assembly of a balloon catheter according to one embodiment of the present invention.

In another embodiment of the present invention, as shown in FIGS. 8 and 9, the above described functionality of the inflation ports 32 is enhanced by employing one or more de-airing channels 102. The de-airing channel 102 is formed in the outer layer 68 of the inner assembly 16. At a minimum, the de-airing channel 102 initiates longitudinally approximate the distal end 90 of the inflation plug 88 and continues uninterruptedly to approximately a proximate end of the air purge port 94. The length of the de-airing channel 102 may extend to or overlap with the distal end 90 of the inflation plug 88 and/or the proximate end of the air purge port 94. The de-airing channel 102 may be either radially aligned or radially offset with the channel 92 of the inflation plug 88 and/or the air purge port 94 relative to an axis through the lumen 22 of the inner assembly 16.

The de-airing channel 102 is formed by placing one of more mandrels having diameters in the range of 0.001 to 0.030 inches between the outer layer 68 of the inner assembly 16 and the heat shrinkable tube and then heating the heat shrinkable tube as described above. In certain embodiments, the de-airing channel 102 is radially aligned with the air purge port 94 and/or with the channel 92 formed in the inflation plug 88. For example, FIG. 9 shows an embodiment in which the de-airing channel 102 is radially aligned with the air purge port 94. The de-airing channel 102 and the air purge port 94 each form a portion of a unified channel. In embodiments in which the de-airing channel 102 is radially aligned with the air purge port 94 and/or with the channel 92 formed in the inflation plug 88, the de-airing channel 102 may extend longitudinally the length of the air purge port 94 and/or may extend longitudinally into or proximately beyond the channel 92 formed in the inflation plug 88.

The de-airing channel 102 helps ensure that a fluid and air flow path is maintained unobstructed between the exterior surface of the inner assembly 16 and the interior surface 96 of the balloon 18. Because the balloon 18 may be closely form fitted over the inner assembly 16 when the balloon is not inflated, absent a de-airing channel 102, it may not always be possible to purge air from lumen 20 of the outer assembly 14 without inflating the balloon 18. Hence, the de-airing channel 102 provides a recess or unobstructed channel on the exterior surface of the inner assembly 16 that allows the passage of air and fluid between the deflated balloon and the exterior surface of the inner assembly 16. Hence, air may be purged from the balloon catheter 10 without inflating of the balloon 18.

It is also contemplated that the de-airing channel 102 may take the form of one or more spiral channels or grooves, spiral ridges, and/or longitudinal ridges on the exterior surface of the inner assembly 16. The de-airing channel 102 may also take the form of one or more small tubular elements bonded to the exterior surface of the inner assembly 16.

Different additional embodiments of the purge ports are also contemplated in connection with any of the previously described embodiments of this specification. It should be noted that while the term purge port is used, this term may include an elongated passage through the device, as well as a port exiting the device. In the following embodiments shown in FIGS. 12-18, the purge port is located at the distal end of the balloon 18, and connects a distal portion of the balloon 18 to the distal tip 30 of the catheter 10. Thus, all the purging is performed at the distal portion of the balloon catheter 18. The inflation lumen remains located proximal to the balloon 18, and thus the balloon 18 is inflated from the proximal end while all the purging is performed at the distal section of the balloon 18. As described in the following embodiments, the purge port 94 remains open initially to purge air from the balloon 18 during a first, preparation stage; and then the purge port is sealed in a second, operational state to prevent the balloon from leaking when the balloon is used in an interventional procedure.

One embodiment includes a swellable material along with the previously described purge port arrangement. It may be desirable to selectively allow the purge port to remain open to purge air, but to close upon exposure to liquid (such as saline or contrast agent, used to flush the air from the purge port) to keep the balloon inflated over time. In one example, the user flushes the system with contrast agent to expel air from the purge port to prep the balloon for use. Contrast agent is also used to inflate the balloon. Thus, once the air is purged from the purge port, the purge port closes to prevent contrast agent from later escaping once additional contrast agent is later introduced to inflate the balloon (i.e. once the balloon is in the body and the interventional procedure is undertaken).

One such embodiment that addresses this issue includes a swellable material either on the purge port itself or adjacent to the purge port. A hydrophilic material swells upon exposure to liquid (i.e. saline or contrast agent) and thus close the purge port lumen once the relevant section of the purge port was exposed to the liquid. Thus, the purge port stays open as air is expelled through the port, but once the distal purge port contacts the liquid (meaning the air is almost completely flushed from the system), the purge port will start to swell and eventually contract, blocking the liquid from being expelled.

Figure 12:
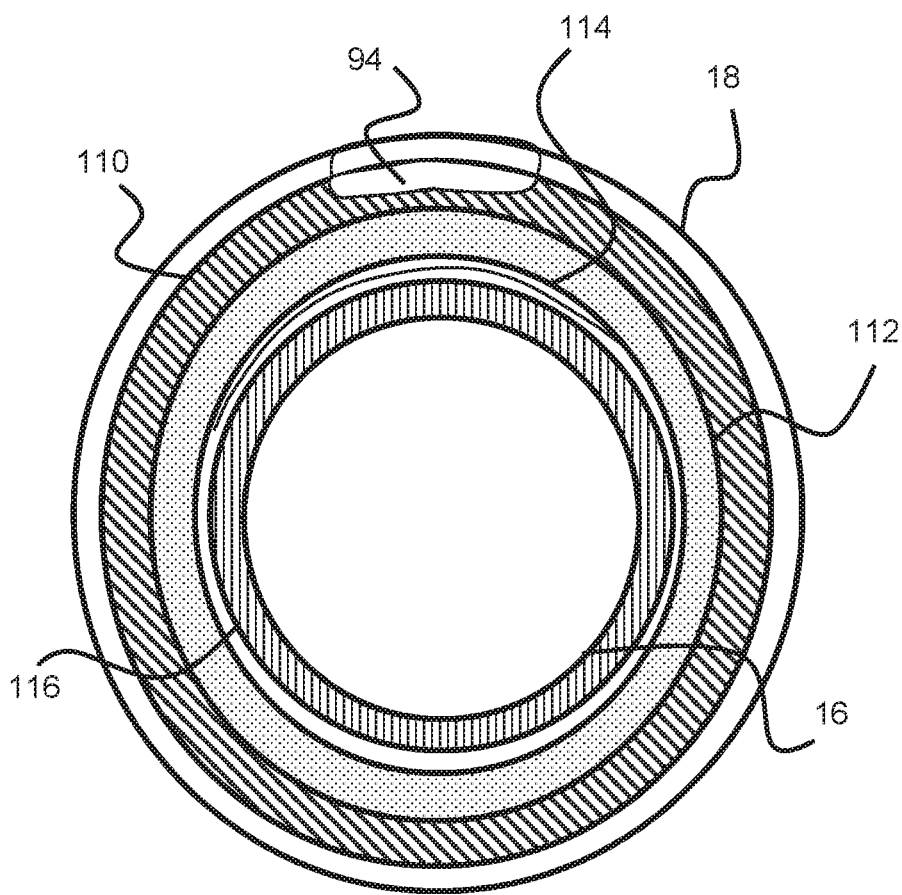
FIGS. 12-18 show various embodiments of an air purging system that can be used in a balloon catheter.

The swellable material may be located adjacent the purge port or may physically comprise a distal section of the purge port. FIG. 12 shows such a system, utilizing a swellable material adjacent the purge port. Specifically, FIG. 12 illustrates a cross section near the distal end of the balloon 18, where the purge port 94 spans a distal portion of the balloon 18. The swellable layer 110 is located under purge port 94, in addition to optional additional liner layers 112, 114, 116, which can be located between guidewire lumen 16 and swellable layer 110. Alternately, the swellable material can be used with any of the prior embodiments.

As previously discussed, alternative configurations may position the swellable material on a distal section of the purge port 94, thereby allowing the purge port to contract upon exposure to liquid instead of having an adjacent surface compressing the purge port. Alternatively, the entirely of the purge port 94 itself may utilize the swellable material. Any hydrophilic material can be used in the swellable layer, such as rubber or hydrogel.

In another embodiment, the purge port 94 is collapsible. In one embodiment, the purge port 94 remains in an otherwise open configuration but collapses in response to a stimulus (such as aspiration or a vacuum). The user prepares the balloon 18 by introducing an agent (e.g., saline or contrast agent) to clear the air from the balloon 18. Next, the user introduces a vacuum or aspiration source which causes the purge port 94 to collapse and thereby shut. Later in the procedure, when the balloon 18 is positioned in the body, the purge port 94 will remain sealed and the inflation media (i.e. contrast agent) will not escape, preventing the balloon 18 from leaking over time.

A soft, tacky, and collapsible material can be used to create the purge port 94 to enable the port to easily collapse. An elliptical cross sectional shape may also be desirable for such a system so that the minor axis of the ellipse requires only minor movement to collapse completely, although a more rounded shape may also be used where the purge port walls are composed of a relatively weak polymer material that allows easy collapse. Additional cross sectional shapes, such as a "D" or "C" shape, are also possible. In these example shapes, the flat side of the "D" shape or the open portion of the "C" shape can be oriented such that they are either facing a direction toward the guidewire lumen 16 or facing away from the guidewire lumen 16 (i.e., facing "downward" or "upward" in the example cross section of FIG. 12).

Figure 13:
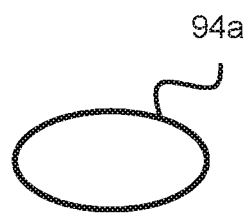
Figure 14:
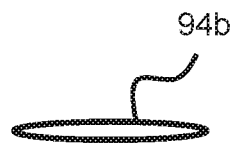

In one example, the entire length of the purge port 94 is collapsible. In another example, only a section of the purge port 94 is collapsible. This collapsible section may be accomplished by a variety of methods, such as creating a weakened wall region in a section of the length, allowing that section to easily constrict. FIGS. 13-14 show a collapsible purge port in which the purge port has a first open configuration 94a when the purge port is open to purge the system, and the purge port subsequently adopts a second closed configuration 94b once vacuum or aspiration is used to close the purge port 94.

In another embodiment, the purge port 94 includes a restricting member positioned at or past the proximal end of the purge port 94 to block flow at the proximal part of the purge port 94 once the balloon 18 has been collapsed over the purge port, thereby preventing over-aspiration. This restricting member may be a wall region having an increased thickness and located at the proximal end of the purge port 94 to block the purge port lumen. This restricting member can also be described as a bump or protruding region.

Figure 15:
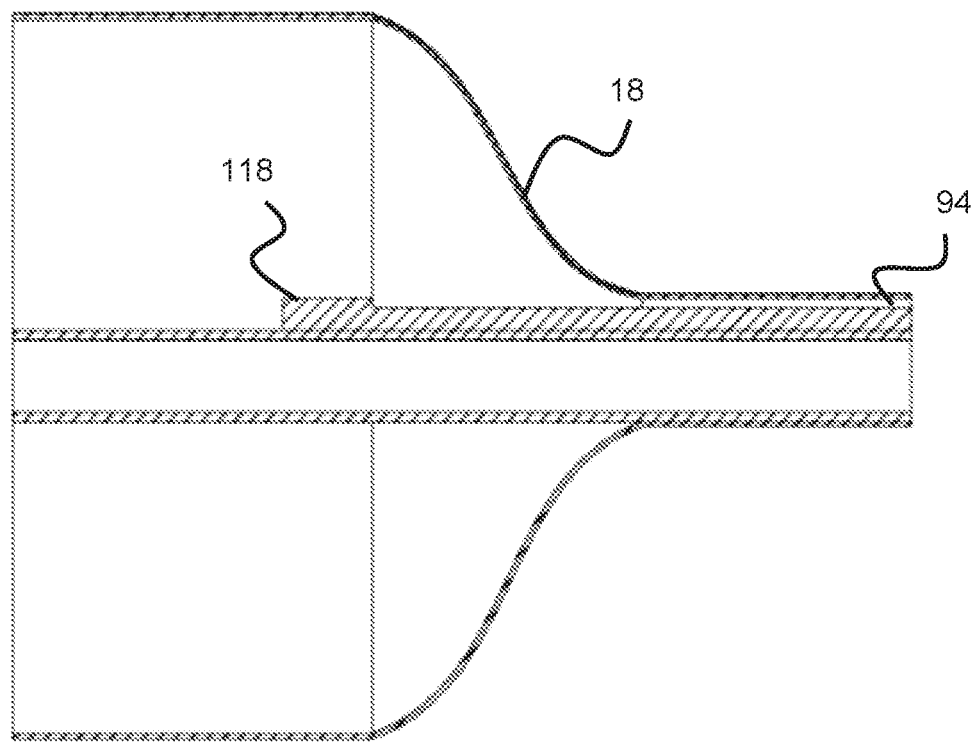
Figure 16:
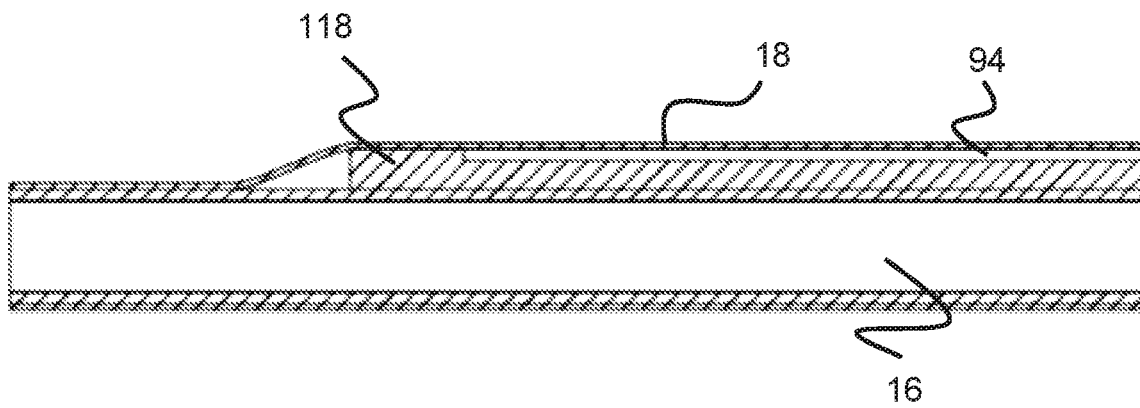

In operation, the user aspirates to deflate the balloon, and since over-aspiration is undesirable since blood could be introduced into the system if aspiration continues after the balloon is deflated, the bump seals the purge port 94. This is shown in FIGS. 15-16, where the right side represents the distal end of the balloon and the purge port spans between a distal section of the balloon and the distal tip of the balloon. In FIG. 15, the balloon is inflated and bump 118 does not impede the flow since the balloon is inflated and there is space for the fluid to pass. FIG. 16 shows the condition when the balloon is deflated, such as after the user has aspirated the balloon to deflate it. Bump 118 now blocks the flow path, so once the balloon is completely deflated, further aspiration or suction is not possible.

In another embodiment, the purge port 94 seals itself when the balloon is fully inflated, to prevent any leakage from the balloon 18. In this embodiment, the distal section of the purge port is integral with the distal portion of the balloon wall. Thus, the balloon wall itself contains a lumen which defines the purge port. This may be made in a number of ways, for example, the purge port may be first constructed and then the balloon can be built over the purge port passage so that the purge port is incorporate into the distal section of the balloon when making the balloon, so that the distal portion of the balloon includes the purge port incorporated into its wall. Alternately, the balloon can be built and then a lumen can be introduced into the balloon, wherein the lumen would define the purge port. The wall of the balloon will stretch and will thin as the balloon inflates. This stretching and thinning action will compress the purge port lumen, which is incorporated into the balloon wall, causing the purge port lumen to close. Thus, when the balloon is fully inflated, the purge port will close preventing any leakage.

Figure 17:
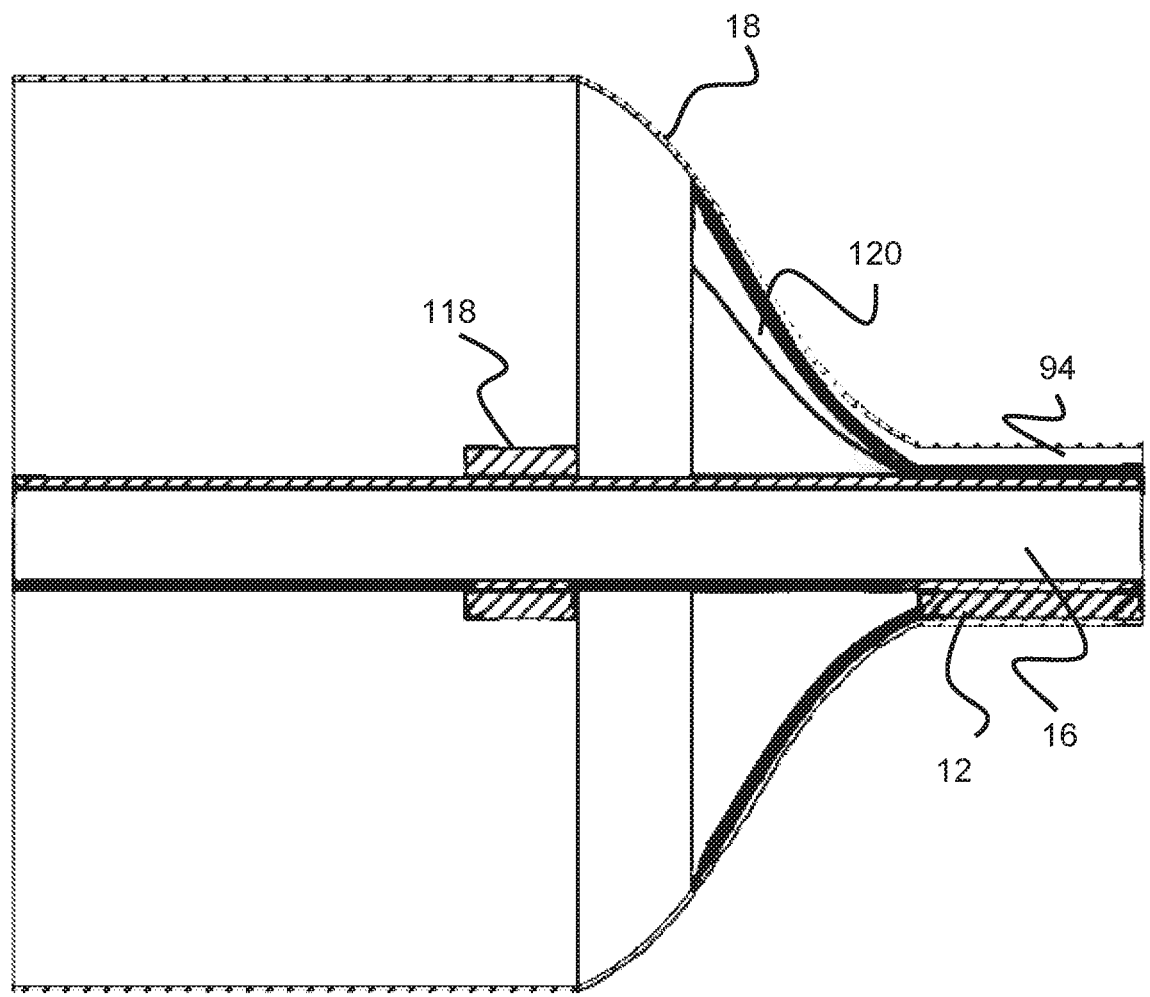
Figure 18:
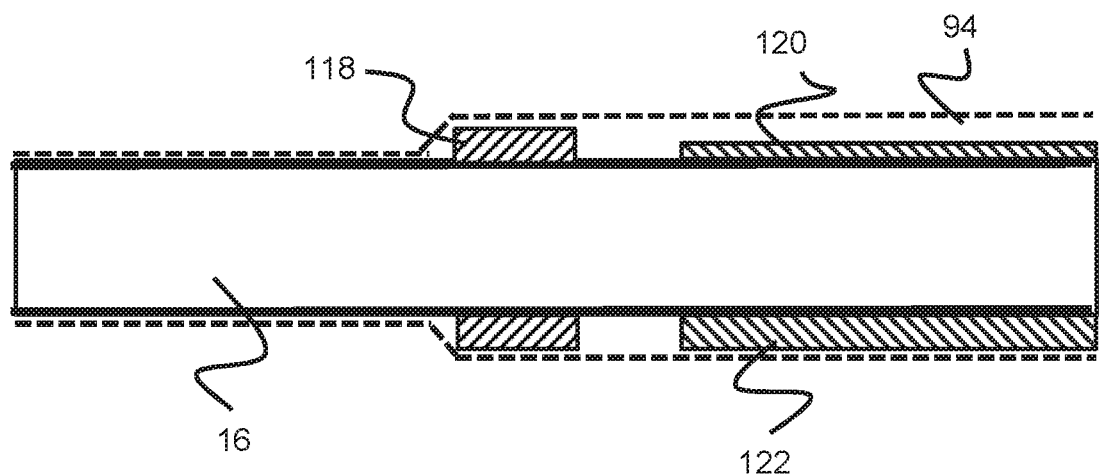

Similar to the compressible purge port embodiment above which utilized an elliptical, or C-shaped, or D-shaped cross sectional purge port shape to aid the self-closing of the purge port, this embodiment may also utilize such a shape. A reinforcing band may also optionally be utilized to create a choke point on the distal section of the balloon. This reinforcing band attaches to the balloon. As the balloon expands, the band applies force on the section of the purge port lumen directly under the band since the distal purge port lumen is integrated into the balloon wall, which creates a choking point and closes the lumen. This embodiment may, optionally, also utilize the bump feature of FIGS. 15-16 to create a system that would prevent balloon leakage when the balloon is inflated as well as prevent over-aspiration once the balloon is deflated (via the bump mechanism). FIG. 17-18 shows the embodiment contemplated here. Purge port 94 is shown, and is integral with the balloon 18 wall. In one example, the balloon 18 utilizes liners 120, 122 which connect to part of the purge port. As the balloon 18 expands, the liners compress against the purge port 94 causing the purge port to close (as shown in FIG. 17, where the proximal section of purge port 94 tapers down to the point it is completely shut). When the balloon is deflated as shown in FIG. 18, the purge port 94 opens and bump 118 prevents over-aspiration, similar to the embodiment described earlier. Alternative configurations may solely utilize the band element or the natural expansion of the balloon and the related decreasing wall thickness to close the purge port.

Figure 10:
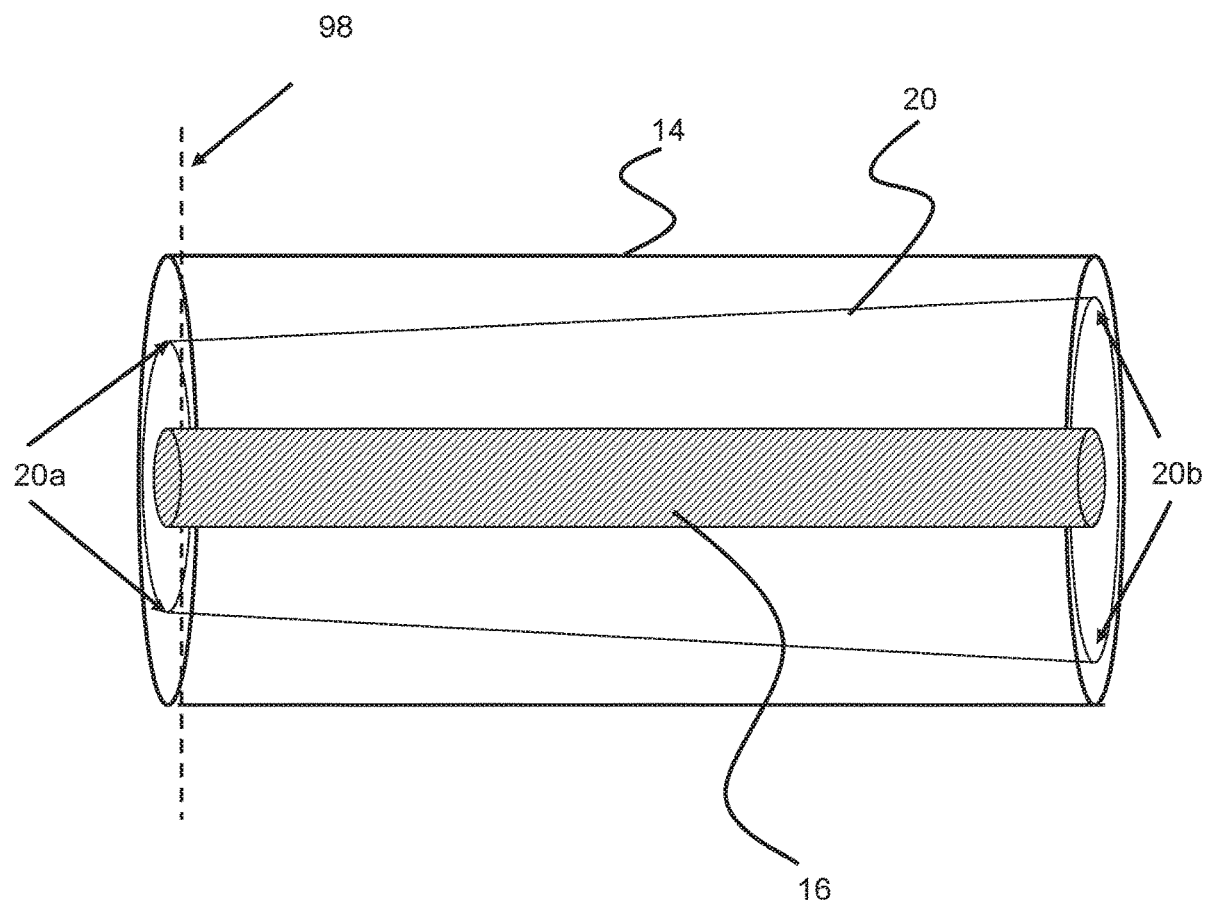
FIGS. 10-11 show a longitudinal view of tapered outer lumen of a balloon catheter according to one embodiment of the present invention.

In another embodiment, the inner diameter of the outer assembly may be tapered from the proximal to the distal end of the catheter, as shown in FIG. 10. This taper will result in a tapered inflation lumen. Position 98 indicated by the dashed line is similar to the distal end of the outer assembly indicated by position 98 in FIG. 2. Inner assembly 16 is the guidewire lumen of the earlier figures. In one example, the lumen diameter 20a at position 98 is within the range of 0.02"-0.03", and in in one more specific example 0.0293". In one example, the lumen diameter 20b at the most proximal position of the balloon catheter is in the range of 0.03"-0.035", in one more specific example 0.0305".

The tapered lumen can be produced by utilizing a tapered mandrel to form outer assembly 14, said tapered mandrel would result in a tapered inner diameter/lumen. The use of a taper means the proximal portion of the balloon catheter has a thinner structural layer and larger inflation volume than the more distal portion of the balloon catheter, which has a thicker structural layer and smaller inflation area. This difference in inflation volume is particularly beneficial for deflation of the balloon, where the higher proximal volume allows for greater suction pressure than would be otherwise possible with a consistent volumetric profile throughout lumen 20.

Figure 11:
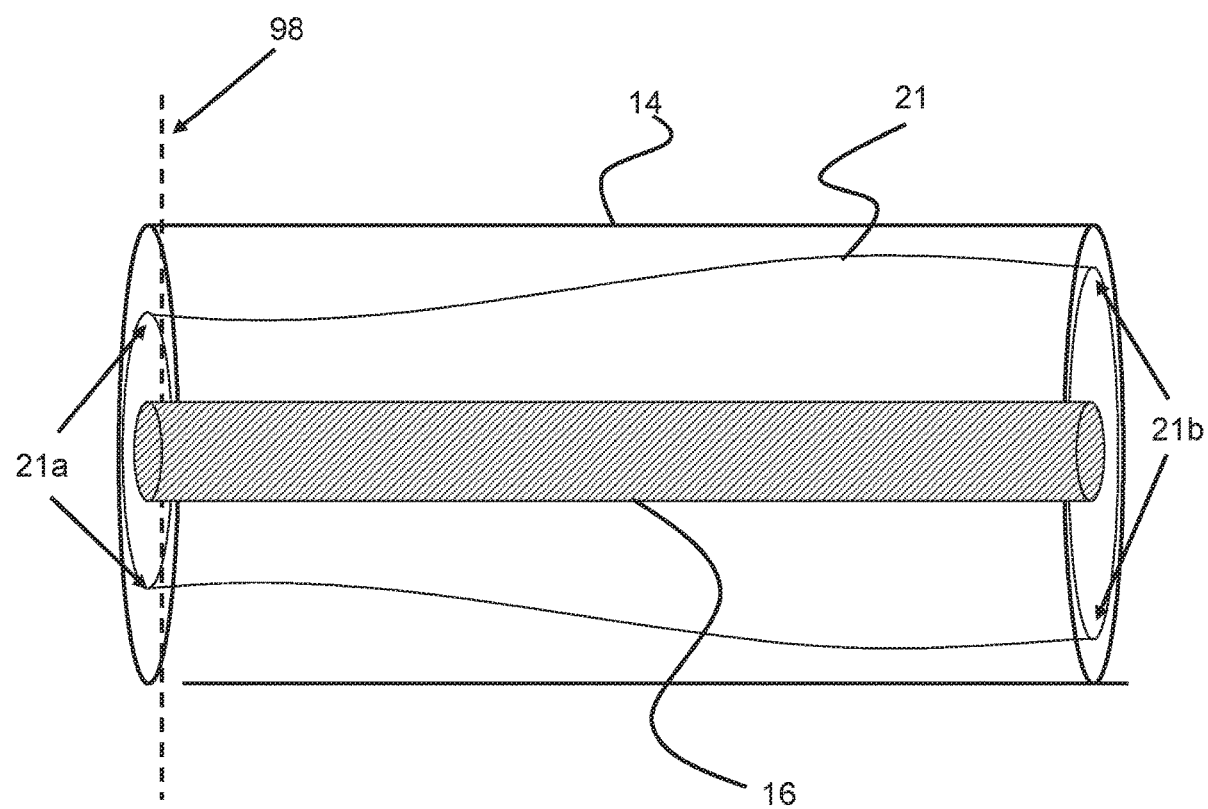

FIG. 11 illustrates another example of a tapered inflation lumen 21. Unlike the example in FIG. 10, inflation lumen 21 utilizes a non-linear taper that is curved from a larger diameter region 21B to a smaller diameter region 21a. Other shapes are also possible. Preferably, the tapered shape lacks sharp edges to prevent any areas where air can get caught and create eddies or turbulence which would negatively affect the deflation time. The inflation lumen shape can be formed by utilizing a shaped mandrel, and thus various shapes are contemplated by utilizing an appropriately shaped mandrel.

Similar to the earlier embodiments described, the tapered inner lumen 21 can comprise a polymer with a higher melt temperature than outer layer 14. The tapered inner lumen 21 can also include a metallic reinforcement layer.

In another embodiment, a tapered inflation lumen is utilized, but the taper is only utilized on a small portion of the lumen. Balloons and balloon catheters used in the neurovasculature typically have a relatively small size due to the smaller blood vessels in this region of the body. A taper is desirable in order to augment suction pressure, however, a continual taper is difficult to achieve given the limited volumetric capacity of the inflation lumen given the smaller size of the catheter due to the smaller neurovasculature blood vessels. Thus, a taper may be used in a limited portion of the inflation lumen located near the balloon element. In one example the overall inflation lumen length is 60-70 inches, and the taper exists in about 1-6 inches of the inflation lumen length. In one example, since the taper is limited to a small section of the lumen instead of being distributed throughout the lumen, the transition from the smaller diameter to larger diameter section will be fairly significant.

In another embodiment, both the guidewire lumen 16 and inflation lumen 20 utilize a taper. In one embodiment, the tapers utilized on both lumens extend throughout a substantial length, respectively, or both the guidewire and inflation lumens. In another embodiment, the tapers are present through only a small portion, respectively, of each lumen (i.e. in about 1-6" of overall length). In one example where both guidewire lumen 16 and inflation lumen 20 utilize a taper, the guidewire lumen 16 has a distal section inner diameter (i.e. distal of the taper) of about 0.01-0.015 inches, and a proximal section diameter (i.e. proximal of the taper) of about 0.015 inches. The inflation lumen 20 has a distal section inner diameter (i.e. distal of the taper) of about 0.023 inches and a proximal section diameter (i.e. proximal to the taper) of about 0.027 inches.

It is noted that while the present invention has been described with respect to neurological procedures, it is contemplated that certain features of the present balloon catheter also address needs in non-neurological fields.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A balloon catheter comprising:
a balloon attached to a distal portion of a tubular member;
the tubular member having an inflation lumen in communication with the balloon;
an inner guidewire tube having an inner lumen that accommodates a guidewire which passes through and extends distally beyond the inner lumen; and,
a purge passage extending between an interior of the balloon and an exterior of the balloon catheter; wherein a first interior surface of the purge passage is a distal uninflatable portion of the interior of the balloon and a second interior surface of the purge passage is a swellable material surface;
the purge passage having a first open configuration to allow movement of fluid through the purge passage to an exterior of the balloon catheter; and a second closed configuration to prevent movement of fluid through the purge passage.

2. The balloon catheter of claim 1, wherein the purge passage has an elliptical shape when in the first open configuration.

3. The balloon catheter of claim 1, wherein when an entirety of the purge passage is closed when in the second closed configuration.

4. The balloon catheter of claim 1, wherein a particular section of the purge passage is closed when in the second closed configuration.

5. The balloon catheter of claim 1, wherein the swellable material surface is a hydrophilic material.

6. The balloon catheter of claim 1, wherein the swellable material surface swells upon exposure to liquid.

7. A balloon catheter comprising:
a balloon attached to a distal portion of a tubular member;
the tubular member having an inflation lumen in communication with the balloon;
an inner guidewire tube having an inner lumen that accommodates a guidewire which passes through and extends distally beyond the inner lumen; and,
a purge passage extending between an interior of the balloon and an exterior of the balloon catheter; wherein a first portion of an interior surface of the purge passage is a distal uninflatable portion of the interior of the balloon and a second portion of the interior surface of the purge passage is a swellable material surface;
the purge passage having a first open configuration to allow movement of fluid through the purge passage to an exterior of the balloon catheter; and a second collapsed configuration to prevent movement of fluid through the purge passage.

8. The balloon catheter of claim 7, wherein the purge passage has an elliptical shape when in the first open configuration.

9. The balloon catheter of claim 7, wherein the purge passage has a C or D cross-sectional shape when in the first open configuration.

10. The balloon catheter of claim 7, wherein the purge passage has a length, and an entire length of the purge passage is collapsed when in the second collapsed configuration.

11. The balloon catheter of claim 7, wherein only a section of the purge passage is collapsed when in the second collapsed configuration.

12. A balloon catheter comprising:
   a balloon attached to a distal portion of a tubular member;
   the tubular member having an inflation lumen in communication with the balloon;
   an inner guidewire tube having an inner lumen that accommodates a guidewire which passes through and extends distally beyond the inner lumen; and,
   a purge passage extending between an interior of the balloon and an exterior of the balloon catheter; wherein an upper interior surface of the purge passage is a distal uninflatable portion of the interior of the balloon and a bottom interior surface of the purge passage is a swellable material surface;
   the purge passage having a first open configuration to allow movement of fluid through the purge passage to an exterior of the balloon catheter; and a second swelled configuration to prevent movement of fluid through the purge passage.

13. The balloon catheter of claim 12, wherein the swellable material surface swells upon exposure to liquid.

14. The balloon catheter of claim 12, wherein the swellable material surface is hydrophilic.

* * * * *